United States Patent [19]

Keller et al.

[11] 4,237,905

[45] Dec. 9, 1980

[54] AUTOMATIC TYMPANOMETRIC TESTING MEANS

[75] Inventors: James E. Keller, Milford; Irwin Klar, Hudson, both of N.H.

[73] Assignee: Electro Audio Dynamics, Inc., Great Neck, N.Y.

[21] Appl. No.: 62,534

[22] Filed: Jul. 31, 1979

[51] Int. Cl.³ .............................................. A61B 5/12
[52] U.S. Cl. ..................................... 128/746; 179/1 N
[58] Field of Search ......................... 128/746; 179/1 N

[56] References Cited

U.S. PATENT DOCUMENTS

| | | | |
|---|---|---|---|
| 3,757,769 | 9/1973 | Arguimbau et al. | 128/746 |
| 3,949,735 | 4/1976 | Klar et al. | 128/746 |
| 4,002,161 | 1/1977 | Klar et al. | 128/746 |
| 4,009,707 | 3/1977 | Ward | 128/746 |

*Primary Examiner*—Kyle L. Howell
*Attorney, Agent, or Firm*—Alexander C. Wilkie

[57] ABSTRACT

An improved tympanometric testing means is described for automatically testing the status of the middle ear. The testing unit provides a recording on a chart showing a change in the compliance of the middle ear during change of the air pressure in the external ear. The tympanometric test unit operates automatically as the clinician inserts the test probe into the patient's ear. The unit automatically determines that the probe is in an unblocked condition and that the test probe tone is at a proper intensity relative to the ear canal volume. When these conditions are met and the ear canal pressure at the probe reaches the predetermined test start pressure, the unit proceeds with the testing as the pressure in the ear canal moves between desired limits such as between the +200 and −200 mm H₂O and while the recorder makes a plot of the ear drum compliance.

28 Claims, 6 Drawing Figures

AUTOMATIC TYMPANOMETRIC TESTING MEANS

BACKGROUND OF THE INVENTION

The present invention relates to automatic instruments for testing hearing and more particularly to an improved and fully automated instrument for testing the status of the middle ear in a test known as tympanometry.

Tympanometry is an objective method for evaluation of the mobility of the tympanic membrane or eardrum and the functional condition of the middle ear and is the measurement of eardrum compliance change as air pressure is altered in the external auditory canal. These measurements are recorded on a graph which represents the compliance-air pressure function.

The tympanic membrane is at maximum compliance when the air pressure in the middle ear is equal to the air pressure in the external ear canal. Tympanometry provides an indirect measure of existing middle ear pressure by identifying the air pressure in the external auditory canal at which the eardrum shows its maximum compliance.

For example, patients who have intact tympanic membranes with no middle ear pathology and adequate eustachian tube function, will show maximum compliance on the graph at atmospheric pressure or within 50 mm of atmospheric pressure. Patients with intact eardrums and poorly functioning eustachian tubes, will show maximum compliance of other air pressure values.

A probe is first placed in the patients ear which is initially clamped into a position of poor mobility by introducing positive pressure of $+200$ $H_2O$ into the external ear canal. The air pressure in the external ear canal is then systematically reduced while changes in the compliance are observed and recorded. As the air pressure is reduced, the eardrum becomes more compliant. When the air pressure in the external canal is exactly the same as the air pressure in the middle ear cavity, the compliance reaches its optimum.

As the air pressure in the external ear canal is further reduced beyond the point of maximum compliance, an unbalance of air pressure on either side of the tympanic membrane is created and the eardrum begins to show reduced compliance again.

The clinical uses of tympanometry are many since the technique demonstrates abnormalities in the mobility of the tympanic membrane due to stiffness, flaccidity, or the presence of fluid in the middle ear cavity. The technique of tympanometry can be used to monitor healing of tympanic membrane grafts, poststapedectomy cases, or follow-up of otitis media.

The apparatus of the present invention is an improvement upon an tympanometric instrument disclosed in U.S. Pat. No. 4,002,161, issued on Jan. 11, 1977. The improved apparatus of the present invention not only provides for an automated probe pressure change and synchronized compliance recording, but it also further provides for a fully automatic testing cycle. In accomplishing this, the apparatus determines automatically that the probe is properly positioned in the patient's ear without blockage and that a test one in the probe has the proper intensity relative to the blocked-off ear canal volume and further that the air pressure within the blocked-off canal has reached the desired test start level. When the apparatus has made these determinations and found them suitable, the test cycle is automatically commenced and performed and tympanometric recording is generated. At the completion of the testing and recording cycle, the test cycle is automatically terminated and the recording means is reset for the next cycle.

The clinician need only insert the test probe into the patient's ear and keep it in place as the automated test is performed and recorded. Indications of unsatisfactory conditions as to blockage or canal test volume or ear pressure are corrected by probe adjustments and the test is automatically performed as soon as the clinician makes the necessary adjustments. This improves the tympanometric testing by assuring that proper conditions have been obtained, by simplifying the test procedure and by reducing the time for the individual testing and for a test program of a group of patients, particularly where it may be a typical group such as younger school children.

Accordingly, an object of the present invention is to provide an improved automatic tympanometric apparatus.

Another object of the present invention is to provide an automatic tympanometer with an automatic start.

Another object of the present invention is to provide tympanometric apparatus which includes automatic test condition check means and a related automatic test start.

Another object of the present invention is to provide tympanometric test means with an automatic test probe block detector and control means.

Another object of the present invention is to provide tympanometric test means providing reliable results while used by relatively inexperienced testing personnel.

Another object of the present invention is to provide improved tympanometric testing means for use with young children.

Another object of the present invention is to provide visual information to the operator so as to guide the operator as to the proper positioning of the probe. This is a key reason why the instrument is so easy to use and an important function for the automatic test condition check.

Other and further objects of the present invention will be apparent upon an understanding of the illustrative embodiment about to be described or will be indicated in the appended claims, and various advantages not referred to herein will occur to one skilled in the art upon employment of the invention in practice.

BRIEF DESCRIPTION OF THE DRAWINGS

A preferred embodiment of the invention has been chosen for purposes of illustration and description and is shown in the accompanying drawings, forming a part of the specification, wherein:

FIG. 3 is a block diagram illustrating the recorder portion of the system.

FIG. 5 is a functional diagram for the logic portion of the system.

FIG. 6 is a front elevational view of a recording chart for the apparatus of the invention.

DESCRIPTION OF THE PREFERRED EMBODIMENT

Figure 1:
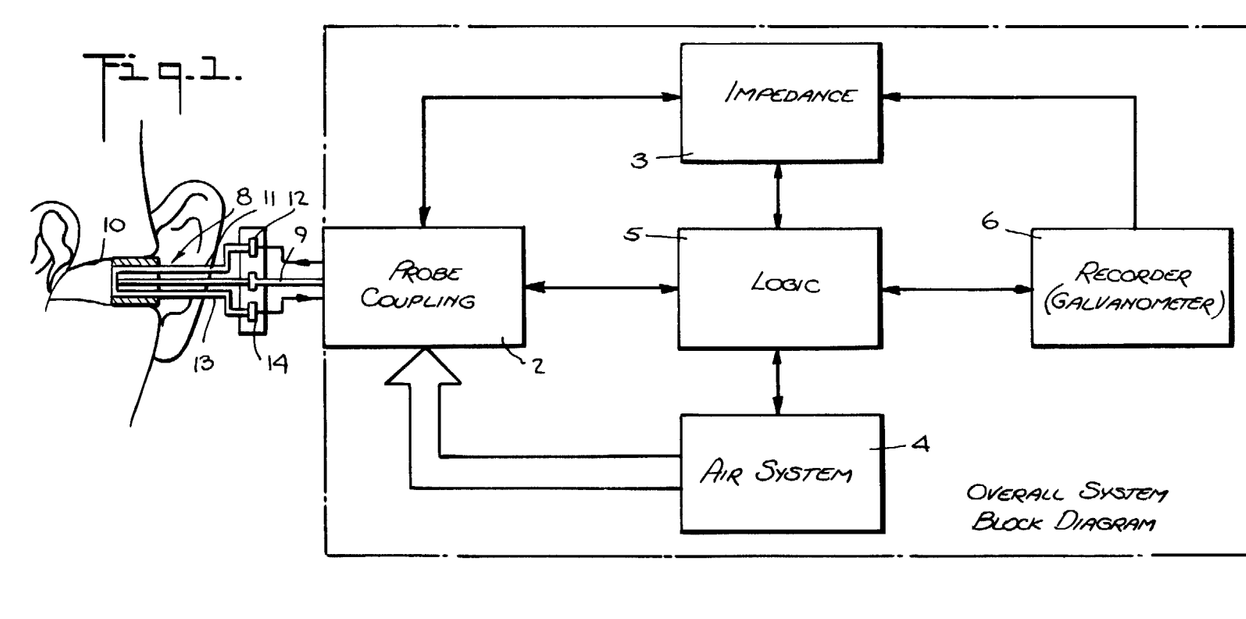
FIG. 1 is a diagrammatic illustration of the elements of the tympanometric means in accordance with the invention.

FIG. 1 illustrates the principal portions of the improved apparatus as used for tympanometry. A suitable cabinet 1 provides a housing for the principal elements which comprise a probe connection 2 which is coupled to an impedance system 3, an air system 4, and a logic system 5 for controlling the impedance and air systems 3 and 4 as well as a recorder 6 such as a galvanometer coupled to the impedance system 3. The air system 4 is provided for generating the air levels applied through a probe 8 to the sealed-off portion of the ear canal as all of the above elements are controlled and synchronized for the automatic test by the logic system 5.

The improved system is conveniently divided into four main sections or systems. For example, the probe 8 is coupled to an impedance system 3 which generates and processes the probe test signal. One output of the impedance system 3 is the test result signal or the compliance signal which is fed to the recorder 6 for providing the record display on the tympanometric chart. The recorder system 6, thus, comprises a second principal portion of the overall system.

A third portion of the system comprises an air pressure control system 4 for subjecting the sealed ear canal to the range of air pressures utilized in the tympanometric testing. This system, as will be more fully described below, provides for a test cycle where the air pressure within the sealed air canal is normally changed during a test cycle from +200 mm to −200 mm H$_2$O.

The fourth section of the system comprises the control or logic system 5 whose function is to coordinate or to synchronize the automatic operations of the impedance, recorder, and air systems during the automatic tympanometric test cycle.

THE TEST PROBE

As already indicated, the tympanometric testing involves the placing of the test probe 8 in the patient's ear to seal off the outer ear canal and to direct the audio test signal into the sealed canal as its air pressure is changed. The particular probe used is not part of the present invention. Suitable probes, for example, are described in U.S. Pat. Nos. 3,882,848, 4,057,051 and 4,122,841, which issued on May 13, 1975, Nov. 8, 1977 and Oct. 13, 1975 respectively.

Described briefly, these probes, as diagrammatically illustrated in FIG. 1, include a first air tube 9 for controlling the air pressure within the sealed ear canal 10, a second tube 11 for transmitting the audio compliance signal from a transducer 12 into the sealed ear canal 10 and a third tube 13 for transmitting the reflected audio signal through a receiver 14 and back to the impedance system 3.

THE IMPEDANCE SYSTEM

Figure 2:
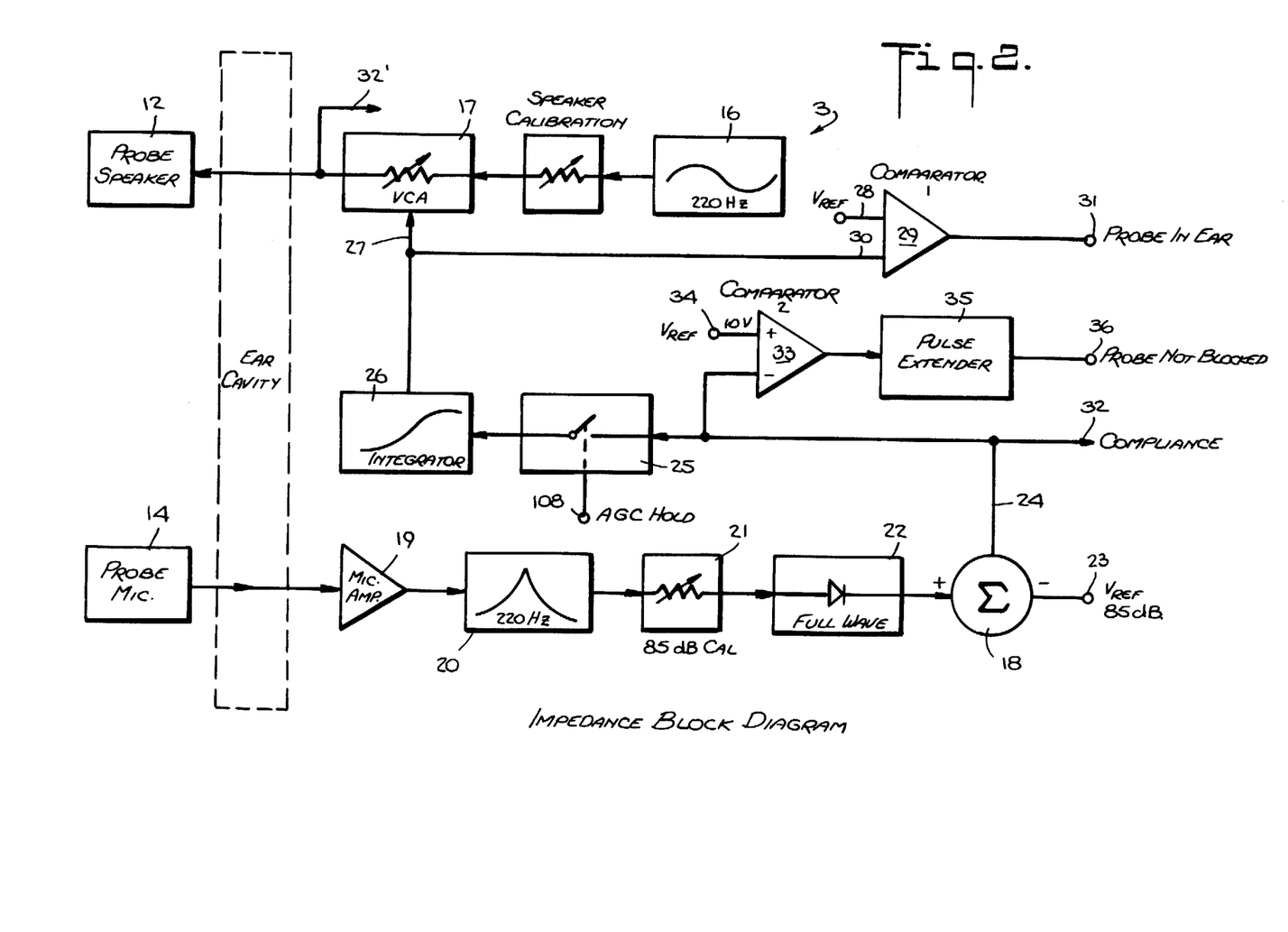
FIG. 2 is a block diagram illustrating the impedance portion of the system.

FIG. 2 illustrates the section of the system identified as the impedance system 3. This portion of the apparatus provides the test signal for the probe 8 and is designed to automatically provide a predetermined signal level at the ear canal 10 for a typical sealed cavity of about one cc within a range of about 0.2 to about 5 cc. A closed feedback loop in the system for this purpose will be described below. In addition, this portion of the system automatically checks for a condition known as a blocked probe which is the condition resulting from improper probe 8 positioning or some other abnormal test probe 8 ear canal 10 relationship. This may occur, for example, where the tip of the probe is adjacent or against the ear canal wall.

As will be further described below, the impedance system 3 includes means for detecting a blocked probe and also means for detecting whether the probe has sealed off a proper cavity within the range of about 0.2 to about 5 cc. A red LED signal will be generated if either of these conditions are detected, and the system will not start the tympanometric run. Additionally, a further no-go condition which is an improper air seal within the sealed air canal also generates a signal preventing the initiation of the tympanometric run and producing a flashing red signal on the same LED. The generation of the flashing LED signal results from a detection of the absence of the required increased air pressure within the sealed canal after the insertion of the probe and the turning on of the pumps in the manner to be described in connection with the description of the air system. In the absence of the sensing of these three no-go conditions, a go signal will be generated in the logic system which is used in the initiation of the tympanometric run and which lights the green LED signal indicating that the tympanometric test is under way.

As seen in FIG. 2, a 220 Hz oscillator 16 is provided which is coupled to the probe speaker 12 through a voltage controlled amplifier 17 which is used in the below described negative feedback loop for setting the desired test signal level in the ear cavity 10. This closed negative feedback loop includes the probe microphone 14 which receives the signal within the ear cavity 10 and is coupled to a summing circuit 18 through an amplifier 19, a bandpass filter 20 centered at 220 Hz, a signal level calibrator 21, and a full wave rectifier 22. The summing circuit 18 is used to establish the desired signal level within the ear cavity by means of the reference voltage input 23. An 85 dB signal level is chosen and this signal is set to provide a zero output on the summing circuit output 24 for an 85 dB condition. The signal on output 24 is fed through an AGC hold switch 25 and a signal averager or integrator 26 back to a control input 27 of the voltage controlled amplifier 17. This feedback is therefore seen to adjust the probe speaker 12 volume for the desired signal level by forming the necessary corrective voltage at the summing network 18 and by feeding it through the integrator 26 to the voltage controlled amplifier 17.

Since the corrective voltage is a function of the size of the ear cavity, this voltage is also used for providing the above mentioned probe-in-ear signals. Voltages within a predetermined range indicate a proper sized cavity. Higher voltages indicate an over large or infinitely large cavity such as results from a failure to properly place the probe in the ear. Thus, the proper range is applied as one input 28 of a comparator 29 with the correction from input 27 feeding voltage to the other comparator input 30.

The comparator 29 provides a signal on output 31 for a cavity less than about 5 cc which is a "yes" signal indicating that a proper cavity has been sealed off and providing one condition for the test go signal and the LED green light signal. During the test cycle, the AGC switch 25 is open so that the signal variations within the ear cavity resulting from the changes in the cavity air pressure are fed from output 24 to the compliance output 32 which feeds the recorder system 6 as will be described below. In an alternative embodiment the AGC switch 25 may be left closed or eliminated and the compliance signal taken from the amplifier 17 output 32'.

The corrective signal from output 24 may also be used to detect a blocked probe since a blocked probe results in a very large signal on the probe microphone. A second comparator 33 having a reference voltage input 34 is connected to the output 24 of the summing circuit for detecting a signal sufficiently large to indicate such a blocked probe, i.e; where the sealed-off cavity is less than about 0.2 cc's. The output of the comparator 33 after being fed through a pulse extender 35 to minimize the ripple effects from the 220 Hz signal is available at a probe-not-blocked signal output 36 for use in the logic system 5 and also to energize a red LED probe-blocked signal advising the clinician that the probe 8 must be adjusted before the tympanometric run can be initiated.

RECORDER SECTION

FIG. 3 illustrates the portions of the system relating to the operation of the recorder or galvanometer 37 for forming the tympanometric chart. The compliance signal which was supplied in the impedance system 3 on the output 32 is fed to the galvanometer 37 through a ripple filter 38, for smoothing the rectified 220 Hz compliance signal, a sensitivity switch means 39, a summing circuit 40, and a power amplifier 41. The sensitivity switch means 39 is illustrated as including three positions which comprise a direct feed through 42 for tympanometric signals, an open contact 43 for zero signal feed and a third contact 44 for a signal sensitivity reducing circuit which includes an amplifier 45. The summing circuit 40 is provided for the purpose of adding an offset signal 46 which is used to pull the galvanometer pen to the zero line on the chart during the recording portions of the cycle. The signal is limited to the recording portions of the cycle by opening the offset switch by offset signal 47 during other times to minimize the energy expended and to thereby minimize heat within the apparatus.

At the lower portion of FIG. 3, a power switch 48 is shown for energizing the recorder drive motor 49. Switch 48 is controlled by the logic circuit coupled to the switch control terminal 50.

At the center portion of FIG. 3, an additional circuit is illustrated which generates a black mark control signal at output 51. The advancing and positioning of the recording paper 52 (FIG. 7) is conveniently controlled through the use of a printed black mark 53 on the paper 52. The circuit detects a mark 53 and generates a black mark signal which is used in the logic together with other conditions and together with the recorder motor switch 48 to position and to advance the recording paper 52 during an automatic tympanometric cycle.

A chopped light signal from a source 54 is directed at the paper 52 and its reflection in the absence of a black mark is detected by a photo transistor 55 which is fed through a filter 56 set at the chopped light frequency to form a control signal through a Schmitt trigger 57 and a pulse extender 58.

The chopped light source is utilized to distinguish the black mark detection from a detection of any random light which may be present in or near the apparatus. When a signal is generated indicating either the presence or the absence of a black mark signal, this signal may be used in the logic system 5 in combination with the recorder motor drive signals for advancing the chart paper in a variety of situations depending upon the particular mode or operation being carried out and where the chart paper is to be positioned pursuant to that particular mode.

THE AIR SYSTEM

As indicated above, an air system is provided for changing the air pressure within the ear canal 10 sealed by the probe 8 from one level to another, for example, from +200 mm to −200 mm during a typical tympanometric test. The probe air tube 9 is coupled to an air reservoir 60 within the instrument and the air pressure within the reservoir 60 is changed in the desired manner by a pressure pump 61 for increased pressure and a vacuum pump 62 for reduced or negative air pressure. A manometer 63 is connected to the reservoir 60 for controlling the operation of the pumps 61 and 62 under the control of the circuits illustrated in FIG. 4.

Since the pressures utilized in tympanometric testing are relatively low and must be precisely controlled and measured, a preferred manometer 63 has an auto zero circuit which reestablishes the zero manometer reading between each cycle. This auto zero includes the negative feedback loop 64 illustrated at the top of FIG. 4. The output voltage or manometer reading is fed to a summing circuit 65 whose output is fed through a manometer slope amplifier 66 to a switched feedback loop 67 which includes an integrator 68 coupled to the negative terminal 69 of the summing circuit 65. When an auto zero switch 70 is closed under the control of the system logic prior to a test cycle, the feedback loop operates to maintain the manometer output at a predetermined voltage from air pressure voltage input 71 which is designated as the "zero pressure" voltage. The output of the slope amplifier 66 is also connected to a second summing circuit 72 for use in the pump control circuit which will now be described.

Figure 4:
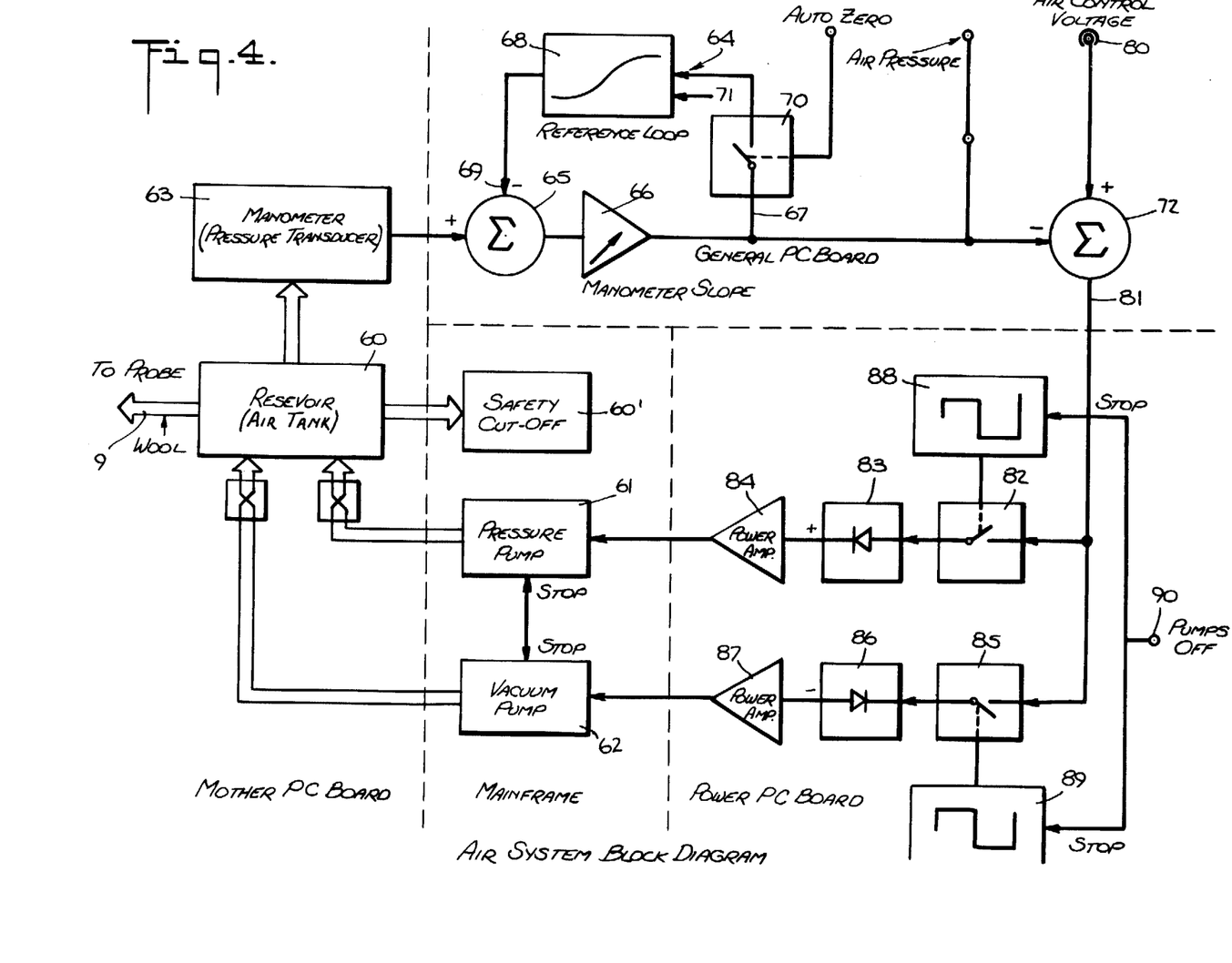
FIG. 4 is a block diagram illustrating the air system portion of the system.
Figure 8:
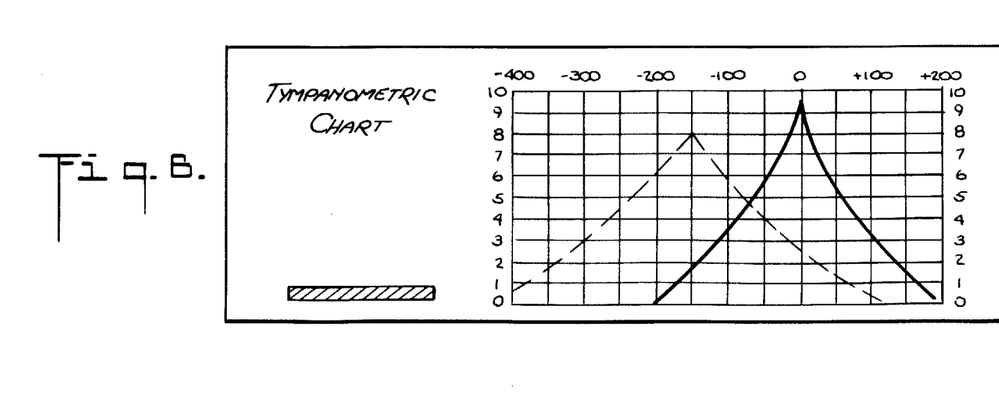
Figure 9:
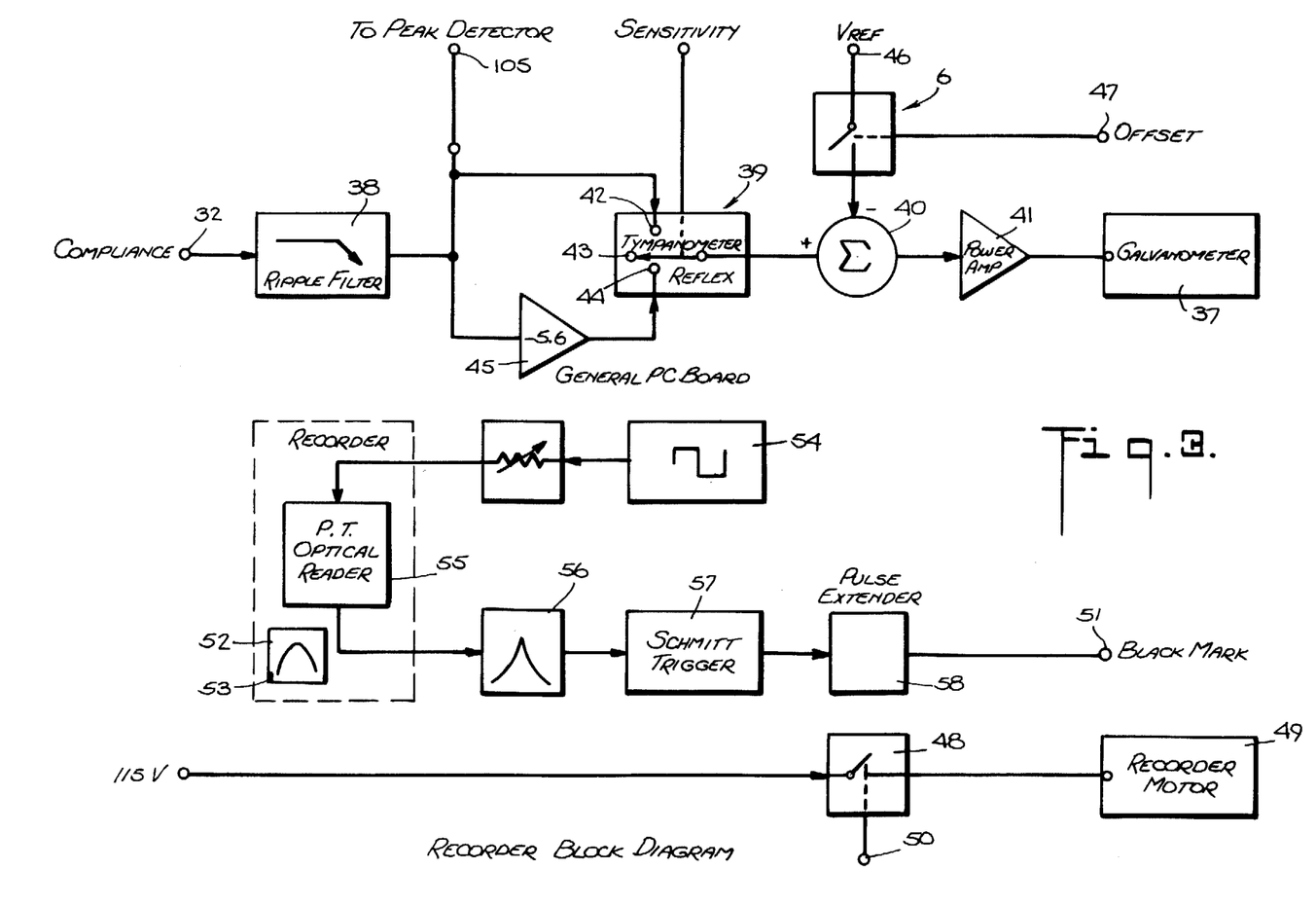

As already indicated, the air system includes a reservoir tank 60 for smoothing its operation and the air pressure within the tank 60 is varied through the desired range by the pressure pump 61 and a vacuum pump 62. The pumps 61 and 62 are each operated by air voltage control circuits.

The air reservoir 60 has its probe output pressure controlled by the action of the pressure pump 61 and the vacuum pump 62. These pumps are under the control of separate activating circuits connected to the summing circuit 72. As already described, the summing circuit 72 has one input which is the manometer 63 air pressure. A second input 80 is an air control voltage supplied in the form of a ramp providing a voltage which originally raises to a voltage equivalent to an air pressure of +200 mm and which then drops along a straight line to a voltage equivalent to a −200 mm pressure. The output 81 of the summing circuit 72 therefore comprises a voltage running between a positive voltage equivalent +200 mm air pressure to a −200 mm air pressure equivalent voltage. The output 81 is connected to separate feed circuits for the pressure pump 61 and the vacuum pump 62. The positive pressure pump line connects through a normally closed stop switch 82 and a positive rectifier 83 and an amplifier 84 to the pressure pump 61. This pump is activated for positive voltages as the voltage output 81 drops from the +200 mm equivalent voltage to the predetermined "zero air pressure" and the corresponding voltage. Thereafter the rectifier 83 acts to cut off this circuit while the increasing negative voltage operates through switch 85 and the negative rectifier 86 and the power amplifier 87 to operate the vacuum pump 62 so that the pressure in the reservoir 60 is dropped in a straight line to the desired −200 mm pressure.

In order to provide for a positive release of pressure and for the positive deactivation of both the pressure and vacuum pumps 61 and 62, the separate pump-off inputs 88 and 89 on the switches 82 and 85 are controlled by the pump-off signal input 90.

Safety valve means 60' is coupled to the reservoir 60 for preventing both an excess pressure or vacuum.

THE LOGIC SYSTEM

FIG. 5 is a diagram illustrating the logic control system which connects the various terminals described for the impedance, air and recorder systems. The automatic logic control system is illustrated using the conventional logic symbols for and gates, or gates, comparators, amplifiers, flip-flops and the like.

The lower portion of FIG. 5 shows the logic system recorder control. Three means are shown for activating the recorder on control 50 which includes a simple manual start switch provided on the housing for energizing an input 91 on the or gate 92 to operate the flop-flop 93. The second means operates through an and gate 94 and the or gate 92 and the flip-flop 93. This comprises an inverse probe in ear signal 31 (probe out of ear) and an inverse black mark signal or input 96 (sensing white) which initiates the recorder movement as soon as a probe 8 is out of the ear to bring the recorder chart 52 up to the black mark registry at which time the recorder will then be turned off preparatory to the start controlled by a proper air pressure etc. The actual test start results from a signal from the second and gate 95 which activates the or gate 92 when there is a combination of the black mark signal 96, the 200 mm air signal on input 97 indicating that the air system is ready for the run and a probe not blocked signal 36. These signals will activate the recorder for generating a tympanometric diagram as the air system goes through its cycle and the probe tones are applied as described above for the impedance system. The red LED showing a no-go condition is also activated through an or gate 98 by a block signal based on the probe not blocked signal 36. The red LED is energized if the probe is blocked and the recording cycle cannot proceed as already described.

At the lower portion of FIG. 5, the logic control for the air system control signals is shown. It includes the air auto zero signal operated by the probe in ear input 31 to operate the above described auto zero switch 70. This circuit includes a one way delay 99 to insure that the pump-off signal has been received and utilized by the pumps when the probe is removed from the ear to insure tank drainage.

It thus is clear, that the red LED is energized at any time that the probe 8 is blocked. There is also a flashing signal indicating that the air has not reached 200 mm even though the probe 8 is in the ear. This flasher 100 is reset or turned off when the proper conditions are present, i.e; by a combination of a black mark signal 96 and a probe in ear signal 31 or the presence of the recorder on signal 50 at the and-or gate network 100'.

A green LED energized from terminal 101 indicates that the system is in the tympanometric mode and that the tympanometric run is under way. The terminal 101 is activated through and gate 102 by a combination of the recorder on signal 50 and a second input from the air system logic indicating that the system is in a tympanometric sensitivity mode.

The AGC hold operating signal 108 for the AGC hold 25 is operated through an or gate 109 from either a manual AGC start signal 118 or a signal from the or gate 110 indicating either a tympanometric sensitivity condition or an inverted black mark signal indicating a white paper or chart advance condition.

The air control voltage 80 is obtained from a ramp generator 111 which is capable of generating voltages corresponding to pressure running from +200 mm to −200 mm under normal conditions and on downwardly to −400 mm under conditions where no peak tympanometric response occurs during the normal run. The ramp generator 111 is activated by the manual start 91 or a black mark signal 51. Its output is fed to the air control voltage terminal thru a switch 112. As long as a peak detector has sensed a peak and made a record of this in the logic system, a comparator 103 having a voltage input 113 representing a −200 mm air pressure terminates the air pressure change and switches the ear pressure for the remainder of the recording to the stored value in storage circuit 107, as controlled by the peak detector 105.

If no peak has been detected, the air control voltage is permitted to run downwardly to the −400 mm pressure level as monitored by a second comparator 114 having the −400 mm voltage input 115. This permits a further tympanometric record on the recorder to complete a tympanometry reading which may be desired even though it is displaced substantially from the normal +200 mm to −200 mm air pressure zone. The chart in this case, is also permitted to continue its movement to a further point which is the reflex point controlled by a comparator 116 having a reflex input 119 and whose output is seen to be connected to the recorder control flip-flop 93 through the or gate 117 which is otherwise controlled by a normal black mark signal 96.

It will be seen that this tympanometric system has been improved for providing an automatic and efficient test cycle. The system and the apparatus embodying the system permit the clinician to merely insert the test probe into the patient's ear to begin the test as soon as the system senses that the proper test conditions are present. If the proper conditions are not present, the probe is adjusted without other apparatus manipulations until the test begins. A further advantage of the tympanometric apparatus of the invention is its ability to continually supply sufficient air pressure or vacuum for the test even though the probe adjustment time may be somewhat longer than normal at the start and may change during the run. This results from a novel continuous air supply system as described above.

As various changes may be made in the form, construction and arrangement of the parts herein without sacrificing any of its advantages, it is to be understood that all matter herein is to be interpreted as illustrative and not in a limiting sense.

What is claimed is:

1. An improved automatic means for tympanometric ear testing under predetermined conditions using an ear probe having means for transmitting and for receiving an audio test signal and having an ear canal seal and an air transmission means and also having a recorder and means for varying the air pressure in the sealed ear canal through said probe air transmission means and means for generating an audio frequency probe tone signal for said transmitting means and means for coupling said probe signal receiving means to said recorder, the improvement comprising means for automatically detecting and evaluating the test conditions and means for automatically controlling the test in accordance with the evaluation.

2. The apparatus as claimed in claim 1 in which said means for automatically controlling the test comprises means for detecting a blocked ear probe condition.

3. The apparatus as claimed in claim 2 in which said means for detecting a blocked probe condition comprises means for evaluating the received probe signal.

4. The apparatus as claimed in claim 1 in which said means for automatically controlling the test comprises means for determining whether the sealed ear canal volume is within a predetermined volume.

5. The apparatus as claimed in claim 4 in which said means for determining the sealed ear canal volume utilizes the received audio probe tone signal.

6. The apparatus as claimed in claim 1 in which said means for automatically controlling the test means comprises means for determining whether the air pressure in the sealed ear canal is at a predetermined level.

7. The apparatus as claimed in claim 1 in which said means for automatically controlling the test includes means for activating the said recorder only when the automatic controlling means indicates that the probe is not blocked and a sealed ear canal of predetermined volume exists and the air pressure within the sealed canal is within a predetermined range.

8. The apparatus as claimed in claim 1 in which said means for automatically controlling the test includes means for detecting an air leak from the ear canal sealed by said probe.

9. The apparatus as claimed in claim 1 in which said means for automatically controlling the test includes means for detecting and for visually indicating a blocked probe.

10. The apparatus as claimed in claim 1 in which said means for automatically controlling the test comprises means for determining and for visually indicating whether the sealed portion of the ear canal is within a predetermined volume.

11. The apparatus as claimed in claim 1 in which said means for automatically controlling the test comprises means for detecting and visually indicating an air leak from the sealed ear canal.

12. The apparatus as claimed in claim 1 in which said means for varying the air pressure in the sealed ear canal comprises an air pump capable of continuous operation.

13. The apparatus as claimed in claim 1 in which said means for varying the air pressure in the sealed ear canal comprises an air pressure pump and an air vacuum pump.

14. The apparatus as claimed in claim 1 in which said means for varying air pressure in the sealed ear canal comprises an air reservoir coupled to said air transmission means in the ear probe and being coupled to an air pressure pump and to an air vacuum pump.

15. The apparatus as claimed in claim 1 in which said means for varying the air pressure in the sealed ear canal includes an automatic zero pressure generating means.

16. The apparatus as claimed in claim 15 in which said zero pressure means comprises a manometer with its output coupled to a summing circuit and with said summing circuit having a portion of its output coupled in a negative feedback reference loop.

17. An improved automatic means for tympanometric ear testing under predetermined conditions using an ear probe having means for transmitting and for receiving an audio test signal and having an ear canal seal and an air transmission means and also having a recorder and means for varying the air pressure in the sealed ear canal through said probe air transmission means and means for generating an audio frequency probe tone signal for said transmitting means and means for coupling said probe signal receiving means to said recorder, the improvement comprising means for automatically detecting and evaluating the test conditions, means for automatically controlling the test in accordance with the evaluation, means for detecting and recording a peak response in the tympanometric test record, means for terminating the test at one negative air pressure reading when a peak is detected and at a more negative air pressure when a peak is not detected.

18. The apparatus as claimed in claim 17 in which said means for varying the air pressure in the sealed ear canal comprises an air pump capable of continuous operation.

19. The apparatus as claimed in claim 17 in which said means for varying the air pressure in the sealed ear canal comprises an air pressure pump and an air vacuum pump.

20. The apparatus as claimed in claim 17 in which said means for varying the air pressure in the sealed ear canal comprises an air reservoir coupled to said air transmission means in the ear probe and being coupled to said air pressure pump and to an air vacuum pump.

21. The apparatus as claimed in claim 17 in which said means for varying the air pressure in the sealed ear canal includes an automatic zero pressure generating means.

22. The apparatus as claimed in claim 21 in which said zero pressure means comprises a manometer with its output coupled to a summing circuit and with said summing circuit having a portion of its output coupled in a negative feedback reference loop.

23. An improved automatic means for tympanometric ear testing under predetermined conditions using an ear probe having means for transmitting and for receiving an audio test signal and having an ear canal seal and an air transmission means and also having a recorder and means for varying the air pressure in the sealed ear canal through said probe air transmission means and means for generating an audio frequency probe tone signal for said transmitting means and means for coupling said probe signal receiving means to said recorder, the improvement comprising means for automatically detecting and evaluating the test conditions, means for automatically controlling the test in accordance with the evaluation, means for detecting and recording a peak response in the tympanometric test record, means for terminating the test at one negative air pressure reading when a peak is detected and at a more negative air pressure when a peak is not detected, and said means for automatically controlling the test including means for activating the recorder only when the test condition evaluation indicates that the probe is not blocked and a sealed ear canal of predetermined volume exists and the air pressure in the sealed canal is at a predetermined pressure.

24. The apparatus as claimed in claim 23 in which said means for varying the air pressure in the sealed ear canal comprises an air pump capable of continuous operation.

25. The apparatus as claimed in claim 23 in which said means for varying the air pressure in the sealed ear canal comprises an air pressure pump and a air vacuum pump.

26. The apparatus as claimed in claim 23 in which said means for varying air pressure in the sealed air canal comprises an air reservoir coupled to said air transmission means in the ear probe and being coupled to an air pressure pump and to an air vacuum pump.

27. The apparatus as claimed in claim 23 in which said means for varying the air pressure in the sealed ear canal includes an automatic zero pressure generating means.

28. The apparatus as claimed in claim 27 in which said zero pressure means comprises a manometer with its output coupled to a summing circuit and with said summing circuit having a portion of its output coupled in a negative feedback reference loop.

* * * * *